United States Patent
Takakuwa et al.

(10) Patent No.: US 11,542,216 B2
(45) Date of Patent: Jan. 3, 2023

(54) ISOMERIZATION OF 1,2-DIFLUOROETHYLENE

(71) Applicant: DAIKIN INDUSTRIES, LTD., Osaka (JP)

(72) Inventors: Tatsuya Takakuwa, Osaka (JP); Osamu Yamamoto, Osaka (JP); Daisuke Karube, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/473,330

(22) Filed: Sep. 13, 2021

(65) Prior Publication Data

US 2021/0403399 A1 Dec. 30, 2021

Related U.S. Application Data

(63) Continuation of application No. PCT/JP2020/040360, filed on Oct. 28, 2020.

(30) Foreign Application Priority Data

Oct. 28, 2019 (JP) .............................. JP2019-194916

(51) Int. Cl.
  *C07C 17/358* (2006.01)
  *C07C 21/18* (2006.01)
  *C07C 17/383* (2006.01)
(52) U.S. Cl.
  CPC .......... *C07C 17/358* (2013.01); *C07C 17/383* (2013.01); *C07B 2200/09* (2013.01)
(58) Field of Classification Search
  CPC .................................................. C07C 17/358
  See application file for complete search history.

(56) References Cited

U.S. PATENT DOCUMENTS

| 2010/0163781 A1* | 7/2010 | Sharratt ............... C09K 5/04 252/67 |
| 2021/0107850 A1 | 4/2021 | Takakuwa et al. |
| 2021/0246090 A1 | 8/2021 | Usui et al. |

OTHER PUBLICATIONS

International Search Report dated Dec. 1, 2020 in International Application No. PCT/JP2020/040360.
Craig et al., "Thermodynamics of cis-trans Isomerizations. The 1,2-Difluoroethylenes", Journal of the American Chemical Society, 1961, vol. 83, pp. 3047-3050.
International Preliminary Report on Patentability dated May 3, 2022 in corresponding International (PCT) Patent Application No. PCT/JP2020/040360.
Abstract of IN 202147000709, corresponds to AA, cited in Office Action dated Jul. 15, 2022 in corresponding IN Patent Application No. 202247028804.
Abstract of IN 202147061861, corresponds to AB, cited in Office Action dated Jul. 15, 2022 in corresponding IN Patent Application No. 202247028804.

* cited by examiner

*Primary Examiner* — Medhanit W Bahta
(74) *Attorney, Agent, or Firm* — Wenderoth, Lind & Ponack, L.L.P.

(57) ABSTRACT

Provided is a method for obtaining HFO-1132(E) and/or HFO-1132(Z) efficiently. The method is a method for producing HFO-1132(E) and/or HFO-1132(Z), comprising supplying a composition containing HFO-1132(E) and/or HFO-1132(Z) to a reactor, and performing an isomerization reaction between HFO-1132(E) and HFO-1132(Z).

19 Claims, 3 Drawing Sheets

Fig. 1 Preferable method for producing HFO-1132(E)

Fig. 2

Fig. 3 Relationship between the reaction temperature and the equilibrium constant for HFO-1132(E/Z)

ISOMERIZATION OF 1,2-DIFLUOROETHYLENE

TECHNICAL FIELD

The present disclosure relates to a method for producing difluoroethylene.

BACKGROUND ART

Non-patent Literature 1 discloses a method for isomerizing HFO-1132(Z) to HFO-1132(E) by contacting HFO-1132(Z) in a gas phase using iodine as a catalyst.

CITATION LIST

Non-Patent Literature

NPL 1: Journal of the American Chemical Society, 1961, vol. 83, 3047

SUMMARY

For example, the present disclosure includes the inventions described in the following items.

Item 1.

A method for producing trans-1,2-difluoroethylene (HFO-1132(E)) and/or cis-1,2-difluoroethylene (HFO-1132(Z)), the method comprising:

supplying a composition containing HFO-1132(E) and/or HFO-1132(Z) to a reactor, and performing an isomerization reaction between HFO-1132(E) and HFO-1132(Z) at a reaction temperature of 600° C. or more.

Advantageous Effects of Invention

According to the present disclosure, HFO-1132(E) and/or HFO-1132(Z) can be obtained efficiently.

DESCRIPTION OF EMBODIMENTS

Conventionally, in the production of HFO-1132(E) and/or HFO-1132(Z), the process of separation by distillation using the differences between the boiling points requires an enormous amount of energy.

This is because HFO-1132(E) (boiling point: −52° C.) has a boiling point close to that of difluoromethane (HFC-32) (boiling point: −51.7° C.), and HFO-1132(Z) (boiling point: −26° C.) has a boiling point close to that of 1,1,2,2-tetrafluoroethane (HFC-134) (boiling point: −20.0° C.).

Accordingly, an object of the present disclosure is to provide a means for solving the above problem. Specifically, an object is to provide a method for producing HFO-1132(E) and/or HFO-1132(Z) more efficiently by lowering the total energy consumption required to separate the two by a combination of isomerization between HFO-1132(E) and HFO-1132(Z) performed by a thermal reaction and distillation using a boiling point difference of 20° C. or more between the two.

The present inventors conducted extensive research to solve the above problem. They found that when a composition containing HFO-1132(E) and/or HFO-1132(Z) is supplied to a reactor, and an isomerization reaction between HFO-1132(E) and HFO-1132(Z) is performed, isomerization is possible (a) at a reaction temperature of 600° C. or more or (b) at a reaction temperature of 200° C. or more in the absence of a catalyst. The inventors also found that the above problem can be solved by a combination of the step of performing an isomerization reaction, and the step of separating a desired isomer. The present disclosure has been accomplished as a result of further research based on these findings. The present disclosure includes the following embodiments.

1. Isomerization Reaction

Figure 1:
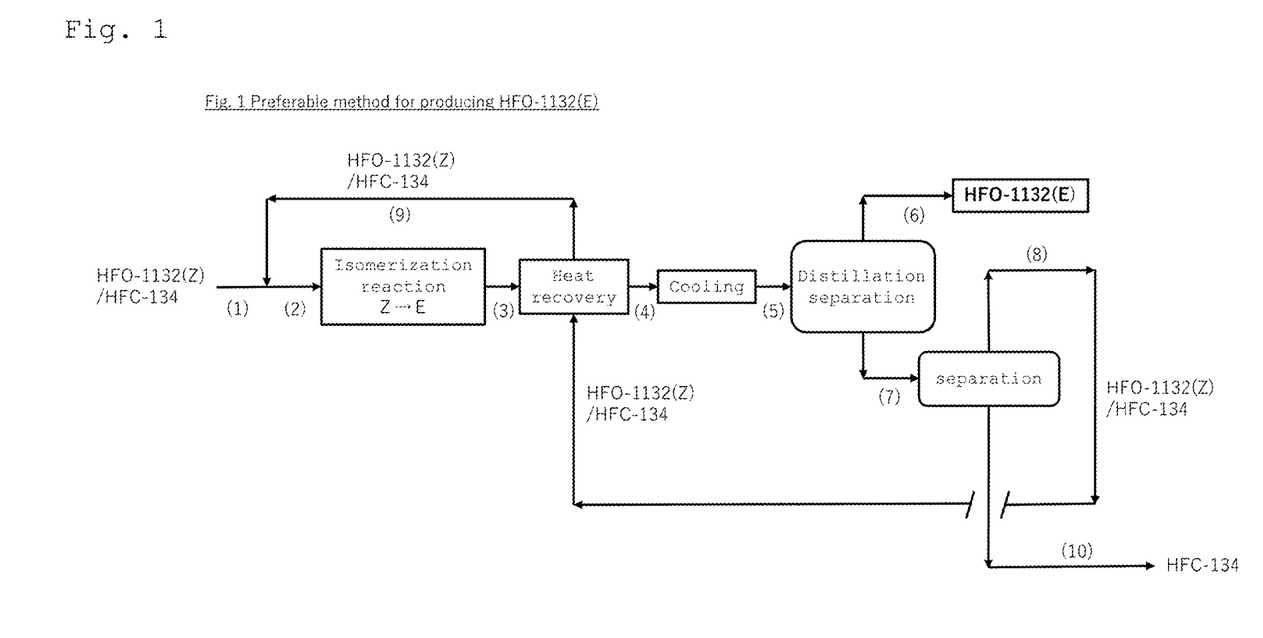
FIG. 1 is a schematic view of a production facility for producing HFO-1132(E) from HFO-1132(Z) efficiently in the method for producing HFO-1132(E) and/or HFO-1132(Z) according to the present disclosure.
Figure 2:
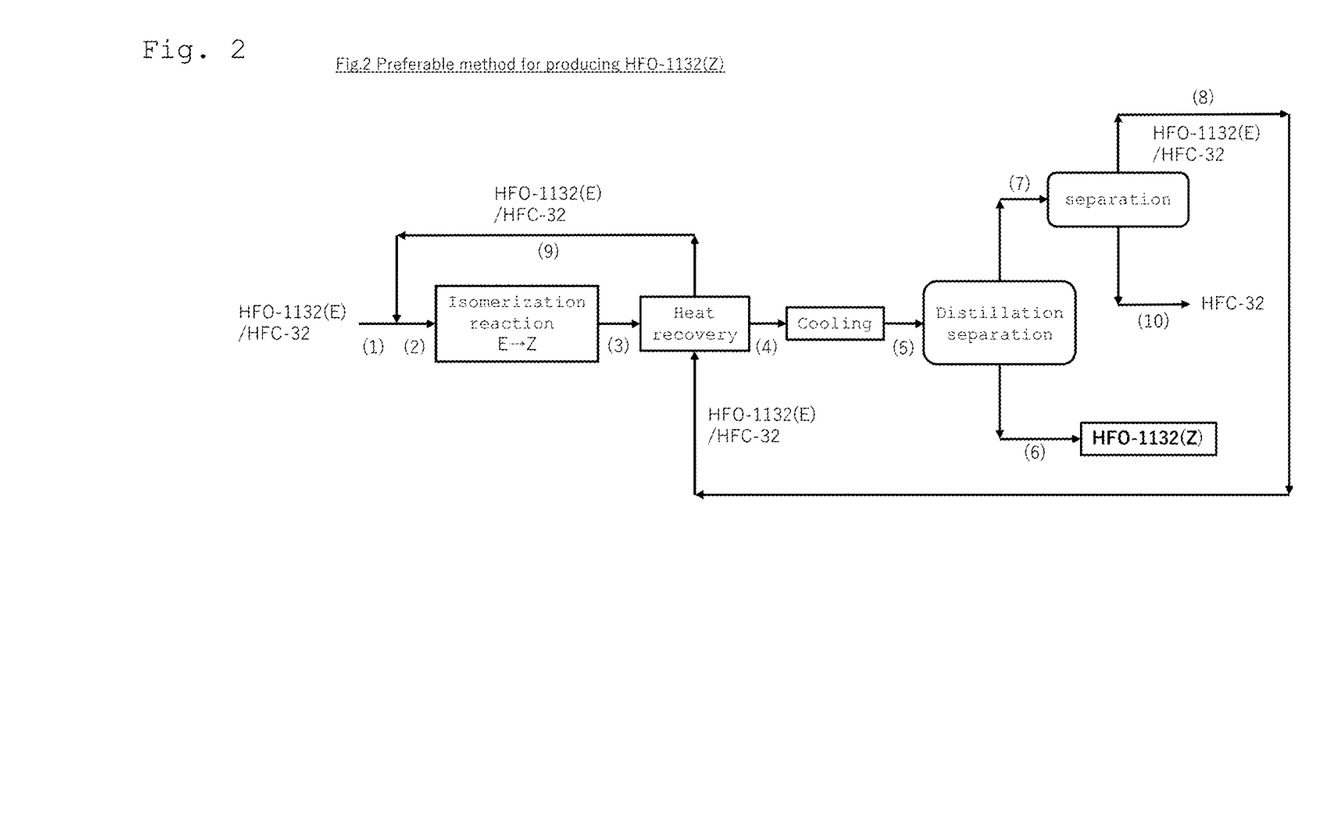
FIG. 2 is a schematic view of a production facility for producing HFO-1132(Z) from HFO-1132(E) efficiently in the method for producing HFO-1132(E) and/or HFO-1132(Z) according to the present disclosure.

The production method according to the present disclosure is a method for producing HFO-1132(E) and/or HFO-1132(Z) in which a composition containing HFO-1132(E) and/or HFO-1132(Z) is supplied to a reactor, and an isomerization reaction between HFO-1132(E) and HFO-1132(Z) is performed at a reaction temperature of 600° C. or more (FIGS. 1 and 2).

The production method according to the present disclosure is also a method for producing HFO-1132(E) and/or HFO-1132(Z) in which a composition containing HFO-1132 (E) and/or HFO-1132(Z) is supplied to a reactor, and an isomerization reaction between HFO-1132(E) and HFO-1132(Z) is performed at a reaction temperature of 200° C. or more in the absence of a catalyst (FIGS. 1 and 2).

In the production method according to the present disclosure, it is preferable that HFO-1132(Z) or a composition containing HFO-1132(E) and HFO-1132(Z) is supplied to a reactor, and HFO-1132(E) is produced in the isomerization reaction.

In the production method according to the present disclosure, it is preferable that HFO-1132(E) or a composition containing HFO-1132(E) and HFO-1132(Z) is supplied to a reactor, and HFO-1132(Z) is produced in the isomerization reaction.

In the production method according to the present disclosure, an isomerization reaction between HFO-1132(E) and HFO-1132(Z) is performed. This isomerization reaction is performed according to the following reaction scheme. Since the E-isomer has a thermodynamic stability lower than that of the Z-isomer, the equilibrium is biased toward the Z-isomer.

In the production method according to the present disclosure, a composition containing HFO-1132(E) or HFO-1132(Z) in varying proportions is obtained by performing an isomerization reaction. In the production method according to the present disclosure, a composition containing an increased proportion of either HFO-1132(E) or HFO-1132(Z) can be obtained by using the equilibrium relationship in the isomerization reaction between HFO-1132(E) and HFO-1132(Z).

Composition Containing HFO-1132(E) and/or HFO-1132(Z)

In the production method according to the present disclosure, the composition containing HFO-1132(E) and/or HFO-1132(Z), which is used as a starting material for isomerization, may contain other components. The other components are not limited as long as they do not significantly impair the isomerization reaction, and can be selected from a wide variety of components.

Examples of other components include impurities mixed in the process of obtaining the composition containing HFO-1132(E) and/or HFO-1132(Z), by-products produced in the process, and the like. The mixed impurities include impurities and the like contained in the starting material.

Examples of the method for obtaining a composition containing HFO-1132(E) and/or HFO-1132(Z), which is used as a starting material, include a method in which a halogenated ethane is subjected to a dehydrohalogenation reaction or a dehalogenation reaction to obtain the composition; and the like.

The halogenated ethane used in the reaction is not limited, and can be selected from a wide range of halogenated ethanes. Specific examples include the following halogenated ethanes and the like. These halogenated ethanes are used in a wide variety of applications, such as refrigerants, solvents, blowing agents, and propellants; and are generally commercially available.

1,1,2-Trifluoroethane ($CHF_2CH_2F$: HFC-143)
1-Bromo-1,2-difluoroethane ($CHFBrCH_2F$)
1-Chloro-1,2-difluoroethane ($CHClFCH_2F$)
1,2-Dichloro-1,2-difluoroethane ($CHClFCHClF$)
1,1,2,2-Tetrafluoroethane ($CHF_2CHF_2$)
1-Chloro-1,2,2-trifluoroethane ($CHClFCHF_2$)

In particular, when HFO-1132(E) is produced in the production method according to the present disclosure, an isomerization reaction from HFO-1132(Z) to HFO-1132(E) is allowed to proceed effectively by using HFO-1132(Z) as a starting material.

In particular, when HFO-1132(Z) is produced in the production method according to the present disclosure, an isomerization reaction from HFO-1132(E) to HFO-1132(Z) is allowed to proceed effectively by using HFO-1132(E) as a starting material.

In the present disclosure, a gas (gas composition) containing HFO-1132(E) can be obtained by subjecting a gas containing one or more fluoromethanes to a reaction involving thermal decomposition (a synthesis reaction involving thermal decomposition of the fluoromethanes).

The gas containing one or more fluoromethanes is preferably at least one fluoromethane selected from the group consisting of chlorodifluoromethane ($CHClF_2$: HCFC-22), chlorofluoromethane ($CH_2ClF$: HCFC-31), difluoromethane ($CH_2F_2$: HFC-32), and fluoromethane ($CH_3F$: HFC-41).

In the production method according to the present disclosure, a gas (gas composition) obtained by subjecting a gas containing at least one fluoromethane selected from the group consisting of HCFC-22, HCFC-31, HFC-32, and HFC-41 to a reaction involving thermal decomposition (a synthesis reaction involving thermal decomposition of the fluoromethane) may be used as a starting material for isomerization. In other words, the production method according to the present disclosure encompasses a method in which after the gas containing one or more fluoromethanes is subjected to a reaction involving thermal decomposition, the resulting gas (gas composition) containing HFO-1132(E) is purified.

The gas containing one or more fluoromethanes is preferably HFC-32 from the viewpoint of reducing the number of steps such as separation of by-products and rectification, and suppressing the formation of hydrocarbon by-products.

The gas containing one or more fluoromethanes preferably has a water vapor content of 1 volume % or less. The selectivity of R1132(E) in the resulting gas containing HFO-1132(E) is improved by using a gas having a water vapor content of 1 volume % or less as the gas containing one or more fluoromethanes. It is preferable that the gas containing one or more fluoromethanes contains no water vapor. It is more preferable that the gas containing one or more fluoromethanes consists essentially of the fluoromethanes.

In the present specification, the term "conversion" refers to, when the target compound is HFO-1132(E), the ratio (mol %) of the total molar amount of compounds other than fluoromethanes contained in the gas (=gas after the synthesis reaction involving thermal decomposition) flowing out of the reactor outlet to the molar amount of fluoromethanes supplied to the reactor.

The term "selectivity" refers to, when the target compound is HFO-1132(E), the ratio (mol %) of the molar amount of the target compound (HFO-1132(E)) contained in the gas (=gas after the synthesis reaction involving thermal decomposition) flowing out of the reactor outlet to the total molar amount of compounds other than fluoromethanes contained in the gas.

The gas containing one or more fluoromethanes may be diluted for use with an inert gas used as a diluent gas. In the gas containing one or more fluoromethanes, the content of at least one inert gas selected from the group consisting of nitrogen, argon, hydrofluorocarbons, and carbon dioxide may be preferably 10 to 90 volume % in terms of improving both the conversion of fluoromethanes and the selectivity of HFO-1132(E).

The hydrofluorocarbon is, for example, at least one member selected from the group consisting of 1,1,2,2-tetrafluoroethane (R134), 1,1,1,2-tetrafluoroethane (R134a), and pentafluoroethane (R125).

The heating method in the reaction involving thermal decomposition may be a known method. The reaction temperature in the reaction involving thermal decomposition is preferably about 750 to 1,050° C., and more preferably about 800 to 900° C., in terms of improving both the conversion of fluoromethanes and the selectivity of HFO-1132(E).

The reaction pressure in the reaction involving thermal decomposition is preferably about 0 to 0.6 MPaG (gauge pressure), and more preferably about 0 to 0.3 MPaG (gauge pressure), in terms of improving both the conversion of fluoromethanes and the selectivity of HFO-1132(E). The lower limit of the reaction pressure can be set to, for example, 0.01 MPaG or 0.1 MPaG.

The reaction time in the reaction involving thermal decomposition can be suitably set depending on the type of fluoromethane, the reaction temperature, the reaction pressure, etc. The reaction time is preferably about 0.2 to 3 seconds, and more preferably 0.5 to 1 second, in terms of promoting the thermal decomposition of fluoromethanes to efficiently obtain HFO-1132(E); and in terms of suppressing side reactions and promoting the thermal decomposition of fluoromethanes to improve the productivity.

The reaction involving thermal decomposition is preferably performed using a metal reactor with an iron content of 10 mass % or less. The reactor is preferably made of a material that is resistant to corrosive action, such as Hastelloy, Inconel, Monel, or Incoloy. Among these reactors, a metal reactor having an iron content of 10 mass % or less, such as a reactor of Hastelloy or Inconel, is more preferably used because it can suppress the occurrence of coking on the reactor inner wall.

Reaction Conditions

In the production method according to the present disclosure, an isomerization reaction between HFO-1132(E) and HFO-1132(Z), i.e., an isomerization reaction from HFO-1132(E) to HFO-1132(Z) or an isomerization reaction from HFO-1132(Z) to HFO-1132(E), is performed at a reaction temperature of 600° C. or more in a reactor, from the viewpoint of suppressing the formation of by-products.

Setting the reaction temperature to 600° C. or more enables the isomerization reaction to proceed rapidly, and allows the equilibrium conversion rate for isomerization to be reached in a short residence time.

When the isomerization reaction is performed at a reaction temperature of 600° C. or more, the reaction is preferably performed in the absence of a catalyst.

In the production method according to the present disclosure, an isomerization reaction between HFO-1132(E) and HFO-1132(Z) is performed at a reaction temperature of 200° C. or more in the absence of a catalyst in a reactor, from the viewpoint of suppressing the formation of by-products.

In the production method according to the present disclosure, when the isomerization reaction is performed at a reaction temperature of 600° C. or more, or when the isomerization reaction is performed at a reaction temperature of 200° C. or more in the absence of a catalyst, the upper limit of the reaction temperature in the isomerization reaction is preferably about 900° C., in terms of increasing the yield of HFO-1132(E) or HFO-1132(Z) and suppressing the decomposition of HFO-1132(E) and HFO-1132(Z) to prevent the conversion to other compounds.

In the production method according to the present disclosure, the reaction time (residence time) of the isomerization reaction is not limited, and can be suitably set. The isomerization reaction can be performed over a wide range of residence times. The residence time is preferably within the range of about 0.1 to 600 seconds, more preferably about 0.2 to 60 seconds, and even more preferably about 0.4 to 10 seconds.

In the production method according to the present disclosure, the pressure in the reactor for the isomerization reaction is not limited, and can be suitably set. A high reaction pressure promotes the formation of a macromolecular compound (polymer) such as tar. Taking this into account, an appropriate pressure can be determined. The pressure may be generally within the range of about ordinary pressure to 0.2 MPaG, and preferably about ordinary pressure to 0.1 MPaG. In the production method according to the present disclosure, the pressure is more preferably within the range of about 0.005 to 0.05 MPaG. In the production method according to the present disclosure, gauge pressure (gauge pressure p: MPaG) is used unless otherwise specified.

Gas-Phase Continuous Flow Mode

In the production method according to the present disclosure, the isomerization reaction is preferably performed in a gas phase. The isomerization reaction is preferably performed in gas-phase continuous flow mode using a tubular reactor as the reactor for performing the isomerization reaction. Performing the isomerization reaction in gas-phase continuous flow mode is economically advantageous because the equipment, operation, etc. can be simplified. When the reaction is performed in flow mode, for example, it is preferable to supply a composition containing HFO-1132(E) and/or HFO-1132(Z), which is used as a starting material for isomerization, to a reactor; appropriately set the reaction temperature in a heater or cooler; and perform the reaction for a certain period of time.

In the production method according to the present disclosure, HFO-1132(E) and/or HFO-1132(Z) can be obtained efficiently by performing the isomerization reaction step in a flow reactor. The isomerization reaction can also be performed in flow mode, in which a starting material is continuously fed to a reactor and the target compound is continuously withdrawn from the reactor.

In the production method according to the present disclosure, when an isomerization reaction between HFO-1132(E) and HFO-1132(Z) is performed, separation of the E-isomer and the Z-isomer is necessary after the isomerization reaction. Thus, the use of a continuous reaction apparatus allows the separation step to also be performed continuously, improving the efficiency of a production facility. For example, by using a distillation column in the separation step, the reaction and the separation can be performed continuously using the continuous reaction apparatus shown in FIG. 1 or 2.

In the production method according to the present disclosure, the isomerization reaction is preferably performed in the presence of a diluent gas. Examples of the diluent gas include oxygen, $N_2$ gas, helium gas, HF gas, argon gas, and the like. In particular, $N_2$ gas is preferable in terms of cost.

To perform the isomerization reaction in the presence of a diluent gas, the diluent gas is preferably supplied to the reactor. The amount of the diluent gas supplied can be suitably set. It is preferable to supply the diluent gas so that the molar ratio of the diluent gas relative to the total amount of HFO-1132(E) and HFO-1132(Z) is 0.01 to 3.0, more preferably 0.1 to 2.0, and even more preferably 0.2 to 1.0.

The gas at the outlet of the reactor may contain HFO-1132a as a by-product, in addition to the target products HFO-1132(E) and HFO-1132(Z). The gas at the outlet of the reactor may further contain unreacted HFC-143, and/or HFC-143a produced by the transition reaction of the starting material.

In Absence of Catalyst

In the production method according to the present disclosure, when an isomerization reaction between HFO-1132(E) and HFO-1132(Z) is performed in a reactor, the reaction is preferably performed in the absence of a catalyst (without using a catalyst). The formation of by-products can be suppressed by performing the isomerization reaction in the absence of a catalyst. The production method according to the present disclosure is a method for producing HFO-1132 (E) and/or HFO-1132(Z) that is economically advantageous; i.e., the method makes it possible to keep the economic cost low, because a catalyst is not essential.

2. Separation Step

The production method according to the present disclosure preferably comprises performing separation into HFO-1132(E) and HFO-1132(Z) by distillation after the isomerization reaction.

The boiling point of HFO-1132(E) (trans form) is −52° C., and the boiling point of HFO-1132(Z) (cis form) is −26° C. In the production method according to the present disclosure, in particular when HFO-1132(E) is produced from HFO-1132(Z), HFO-1132(E) (boiling point: −52° C.) can be efficiently separated from HFO-1132(Z) (boiling point: −26° C.) and HFC-134 (boiling point: −20.0° C.), which is a by-product, by distillation using the differences between the boiling points. This operation enables continuous and efficient production of HFO-1132(E).

In the production method according to the present disclosure, in particular when HFO-1132(Z) is produced from HFO-1132(E), HFO-1132(Z) (boiling point: −26° C.) can be efficiently separated from HFO-1132(E) (boiling point: −52° C.) and HFC-32 (boiling point: −51.7° C.), which is a by-product, by distillation using the differences between the boiling points. This operation enables continuous and efficient production of HFO-1132(Z).

3. Recycling Step

In the production method according to the present disclosure, the stream containing HFO-1132(E) as a main component obtained in the separation step or the stream containing HFO-1132(Z) as a main component obtained in the separation step can be recycled to the isomerization reaction to recover a composition containing an increased proportion of either HFO-1132(E) or HFO-1132(Z).

The production method according to the present disclosure preferably comprises recycling HFO-1132(Z) to the isomerization reaction after the separation step, wherein HFO-1132(Z) or a composition containing HFO-1132(E) and HFO-1132(Z) is supplied to the reactor again, and HFO-1132(E) is produced.

By recycling HFO-1132(Z) as described above, a composition containing an increased proportion of HFO-1132(E) can be obtained in the isomerization reaction after recycling.

The production method according to the present disclosure also preferably comprises recycling HFO-1132(E) to the isomerization reaction after the separation step, wherein HFO-1132(E) or a composition containing HFO-1132(E) and HFO-1132(Z) is supplied to the reactor again, and HFO-1132(Z) is produced.

By recycling HFO-1132(E) as described above, a composition containing an increased proportion of HFO-1132(Z) can be obtained in the isomerization reaction after recycling.

4. Step of Allowing Isomerization Reaction and Separation by Distillation to Proceed Simultaneously In the production method according to the present disclosure, the isomerization reaction and the separation into HFO-1132(E) and HFO-1132(Z) by distillation can be performed simultaneously (reactive distillation). In the production method according to the present disclosure, when an isomerization reaction between HFO-1132(Z) and HFO-1132(E) is performed, the use of a gas-phase continuous reaction apparatus allows HFO-1132(E) or HFO-1132(Z) to be continuously obtained by distillation in an efficient manner while performing the isomerization reaction in a distillation column. This is also economical from a facility viewpoint.

5. Preferable Production Methods Preferable Method for Producing HFO-1132(E) (FIG. 1)

In the production method according to the present disclosure, in particular when HFO-1132(E) is produced from HFO-1132(Z), HFO-1132(E) (boiling point: −52° C.) can be efficiently separated from HFO-1132(Z) (boiling point: −26° C.) and HFC-134 (boiling point: −20.0° C.), which is a by-product, by distillation using the differences between the boiling points. This operation enables continuous and efficient production of HFO-1132(E).

FIG. 1 is a schematic view of a production facility for producing HFO-1132(E) by allowing an isomerization reaction from HFO-1132(Z) to HFO-1132(E) to proceed continuously in an effective manner by using HFO-1132(Z) as a starting material, in particular when HFO-1132(E) is produced in the production method according to the present disclosure.

An isomerization reaction from HFO-1132(Z) to HFO-1132(E) is performed using HFO-1132(Z) as a starting material (1, 2, and 3 in FIG. 1). The starting material may contain HFC-134 in addition to HFO-1132(Z). Subsequently, HFO-1132(Z) and HFO-1132(E) are separated, and heat is recovered (4 in FIG. 1). The gas at the outlet of the reactor after heat recovery is then cooled and liquefied, followed by separation into a stream containing HFO-1132(E) as a main component and a stream containing HFO-1132(Z) as a main component by distillation (5, 6, and 7 in FIG. 1). These operations enable HFO-1132(E) to be continuously produced as a target compound (6 in FIG. 1).

The method comprises, thereafter, recycling HFO-1132(Z) to the isomerization reaction, and subjecting the HFO-1132(Z) to the isomerization reaction again; and HFO-1132(E) is produced (8 and 9 in FIG. 1). The recycling process is performed in this manner, and a composition containing an increased proportion of HFO-1132(E) can be obtained in the isomerization reaction after recycling. These operations make it possible to continuously produce HFO-1132(E).

When the stream containing HFO-1132(Z) as a main component contains HFC-134, HFC-134 is separated by additional distillation or the like (10 in FIG. 1).

Preferable Method for Producing HFO-1132(Z) (FIG. 2)

In the production method according to the present disclosure, in particular when HFO-1132(Z) is produced from HFO-1132(E), HFO-1132(Z) (boiling point: −26° C.) can be efficiently separated from HFO-1132(E) (boiling point: −52° C.) and HFC-32 (boiling point: −51.7° C.), which is a by-product, by distillation using the differences between the boiling points. This operation enables continuous and efficient production of HFO-1132(Z).

FIG. 2 is a schematic view of a production facility for producing HFO-1132(Z) by allowing an isomerization reaction from HFO-1132(E) to HFO-1132(Z) to proceed continuously in an effective manner by using HFO-1132(E) as a starting material, in particular when HFO-1132(Z) is produced in the production method according to the present disclosure.

An isomerization reaction from HFO-1132(E) to HFO-1132(Z) is performed using HFO-1132(E) as a starting material (1, 2, and 3 in FIG. 2). The starting material may contain HFC-32 in addition to HFO-1132(E). Subsequently, HFO-1132(E) and HFO-1132(Z) are separated, and heat is recovered (4 in FIG. 2). The gas at the outlet of the reactor after heat recovery is then cooled and liquefied, followed by separation into a stream containing HFO-1132(Z) as a main component and a stream containing HFO-1132(E) as a main component by distillation (5, 6, and 7 in FIG. 2). These operations enable HFO-1132(Z) to be continuously produced as a target compound (6 in FIG. 2).

The method comprises, thereafter, recycling HFO-1132(E) to the isomerization reaction, and subjecting the HFO-1132(E) to the isomerization reaction again; and HFO-1132(Z) is produced (8 and 9 in FIG. 2). The recycling process is performed in this manner, and a composition containing an increased proportion of HFO-1132(Z) can be obtained in the isomerization reaction after recycling. These operations make it possible to continuously produce HFO-1132(Z).

When the stream containing HFO-1132(E) as a main component contains HFC-32, HFC-32 is separated by additional distillation or the like (10 in FIG. 2).

For example, the present disclosure includes the inventions described in the following items.

Item 1.

A method for producing trans-1,2-difluoroethylene (HFO-1132(E)) and/or cis-1,2-difluoroethylene (HFO-1132(Z)), the method comprising:

supplying a composition containing HFO-1132(E) and/or HFO-1132(Z) to a reactor, and performing an isomerization reaction between HFO-1132(E) and HFO-1132(Z) at a reaction temperature of 600° C. or more.

Item 2.

The method according to Item 1, wherein the isomerization reaction is performed in the absence of a catalyst.

Item 3.

A method for producing trans-1,2-difluoroethylene (HFO-1132(E)) and/or cis-1,2-difluoroethylene (HFO-1132(Z)), the method comprising:

supplying a composition containing HFO-1132(E) and/or HFO-1132(Z) to a reactor, and performing an isomerization reaction between HFO-1132(E) and HFO-1132(Z) at a reaction temperature of 200° C. or more in the absence of a catalyst.

Item 4.

The method according to any one of Items 1 to 3, wherein HFO-1132(Z) or a composition containing HFO-1132(E) and HFO-1132(Z) is supplied to the reactor, and HFO-1132(E) is produced in the isomerization reaction.

Item 5.

The method according to any one of Items 1 to 3, wherein HFO-1132(E) or a composition containing HFO-1132(E) and HFO-1132(Z) is supplied to the reactor, and HFO-1132(Z) is produced in the isomerization reaction.

Item 6.

The method according to any one of Items 1 to 5, comprising performing separation into HFO-1132(E) and HFO-1132(Z) by distillation after the isomerization reaction.

Item 7.

The method according to Item 6, comprising recycling HFO-1132(Z) to the isomerization reaction after the separation step, wherein HFO-1132(Z) or a composition containing HFO-1132(E) and HFO-1132(Z) is supplied to the reactor again, and HFO-1132(E) is produced.

Item 8.

The method according to Item 6, comprising recycling HFO-1132(E) to the isomerization reaction after the separation step, wherein HFO-1132(E) or a composition containing HFO-1132(E) and HFO-1132(Z) is supplied to the reactor again, and HFO-1132(Z) is produced.

EXAMPLES

The present disclosure is described below with reference to Examples; however, the present disclosure is not limited to these Examples.

Example 1

Method for Producing HFO-1132(E) (FIG. 1)

As shown in FIG. 1, HFO-1132(E) was produced from HFO-1132(Z) efficiently. When HFO-1132(E) was produced from HFO-1132(Z) by an isomerization reaction at a reaction temperature of 750° C. without using a catalyst in the production method of Example 1, HFO-1132(E) (boiling point: −52° C.) was efficiently separated from HFO-1132(Z) (boiling point: −26° C.) and HFC-134 (boiling point: −20.0° C.), which is a by-product, by usual distillation using the differences between the boiling points; and HFO-1132(E) was produced continuously and efficiently.

Referring to FIG. 1, the method of Example 1 is described in more detail below.

A composition containing HFO-1132(Z) and HFC-134 was used as a starting material. An isomerization reaction from HFO-1132(Z) to HFO-1132(E) was performed using the composition containing HFO-1132(Z) as a starting material (1, 2, and 3 in FIG. 1). Subsequently, HFO-1132(Z) and HFO-1132(E) were separated, and heat was recovered (4 in FIG. 1). The gas at the outlet of the reactor after heat recovery was then cooled and liquefied, followed by separation into a stream containing HFO-1132(E) as a main component and a stream containing HFO-1132(Z) as a main component by distillation (5, 6, and 7 in FIG. 1). HFO-1132(E) was continuously produced as a target compound by performing these operations (6 in FIG. 1).

Thereafter, HFO-1132(Z) was recycled to the isomerization reaction, and subjected to the isomerization reaction again to produce HFO-1132(E) (8 and 9 in FIG. 1). The recycling process was performed in this manner, and a composition containing an increased proportion of HFO-1132(E) was obtained in the isomerization reaction after recycling. HFO-1132(E) was continuously produced by performing these operations.

Moreover, since the stream containing HFO-1132(Z) as a main component contained HFC-134, HFC-134 was separated by additional distillation (10 in FIG. 1).

Table 1 shows the composition ratio of HFO-1132(E) (target compound), HFO-1132(Z), and HFC-134 in each of lines 1 to 10 in FIG. 1.

Table 1

TABLE 1

| Route | 1 | 2 | 3 | 4 | 5 | 6 | 7 | 8 | 9 | 10 |
|---|---|---|---|---|---|---|---|---|---|---|
| HFC-134 (kg/hr) | 0.42 | 0.42 | 0.42 | 0.42 | 0.42 | 0.00 | 0.42 | 0.42 | 0.42 | 0.54 |
| HFO-1132 (E) target compound (kg/br) | 0.00 | 0.00 | 0.46 | 0.46 | 0.46 | 0.46 | 0.00 | 0.00 | 0.00 | 0.00 |
| HFO-1132 (Z) (kg/hr) | 0.60 | 1.14 | 0.67 | 0.67 | 0.67 | 0.00 | 0.61 | 0.07 | 0.07 | 0.00 |

In the method for producing HFO-1132(E) among the production methods according to the present disclosure, HFO-1132(E) was produced from HFO-1132(Z) continuously and effectively by using HFO-1132(Z) as a starting material.

Example 2

Method for Producing HFO-1132(Z) (FIG. 2)

As shown in FIG. 2, HFO-1132(Z) was produced from HFO-1132(E) efficiently. In the production method of Example 2, when HFO-1132(Z) was produced from HFO-1132(E) by an isomerization reaction at a reaction temperature of 800° C. without using a catalyst, HFO-1132(Z) (boiling point: −26° C.) was efficiently separated from HFO-1132(E) (boiling point: −52° C.) and HFC-32 (boiling point: −51.7° C.), which is a by-product, by usual distillation using the differences between the boiling points; and HFO-1132(Z) was produced continuously and efficiently.

Referring to FIG. 2, the method of Example 2 is described in more detail below.

A composition containing HFO-1132(E) and HFC-32 was used as a starting material. An isomerization reaction from HFO-1132(E) to HFO-1132(Z) was performed using the composition containing HFO-1132(E) as a starting material (1, 2, and 3 in FIG. 2). Subsequently, HFO-1132(E) and HFO-1132(Z) were separated, and heat was recovered (4 in FIG. 2). The gas at the outlet of the reactor after heat recovery was then cooled and liquefied, followed by separation into a stream containing HFO-1132(Z) as a main component and a stream containing as a main component HFO-1132(E) (containing HFC-32) by distillation (5, 6, and 7 in FIG. 2). HFO-1132(Z) was continuously produced as a target compound by performing these operations (6 in FIG. 2).

Thereafter, HFO-1132(E) was recycled to the isomerization reaction, and subjected to the isomerization reaction again to produce HFO-1132(Z) (8 and 9 in FIG. 2). The recycling process was performed in this manner, and a composition containing an increased proportion of HFO-1132(Z) was obtained in the isomerization reaction after recycling. HFO-1132(Z) was continuously produced by performing these operations.

Moreover, when the stream containing HFO-1132(E) as a main component contained HFC-32, HFC-32 was separated by additional distillation (10 in FIG. 2).

Table 2 shows the composition ratio of HFO-1132(E), HFO-1132(Z) (target compound), and HFC-32 in each of lines 1 to 10 in FIG. 2.

TABLE 2

| Route | 1 | 2 | 3 | 4 | 5 | 6 | 7 | 8 | 9 | 10 |
|---|---|---|---|---|---|---|---|---|---|---|
| HFC-32 (kg/hr) | 0.80 | 0.80 | 0.80 | 0.80 | 0.80 | 0.00 | 0.80 | 0.00 | 0.00 | 0.80 |
| HFO-1132 (E) (kg/hr) | 0.30 | 0.51 | 0.21 | 0.21 | 0.21 | 0.00 | 0.21 | 0.21 | 0.21 | 0.00 |
| HFO-1132 (Z) target compound (kg/hr) | 0.00 | 0.00 | 0.30 | 0.30 | 0.30 | 0.30 | 0.00 | 0.00 | 0.00 | 0.00 |

In the method for producing HFO-1132(Z) among the production methods according to the present disclosure, HFO-1132(Z) was produced from HFO-1132(E) continuously and effectively by using HFO-1132(E) as a starting material.

Figure 3:
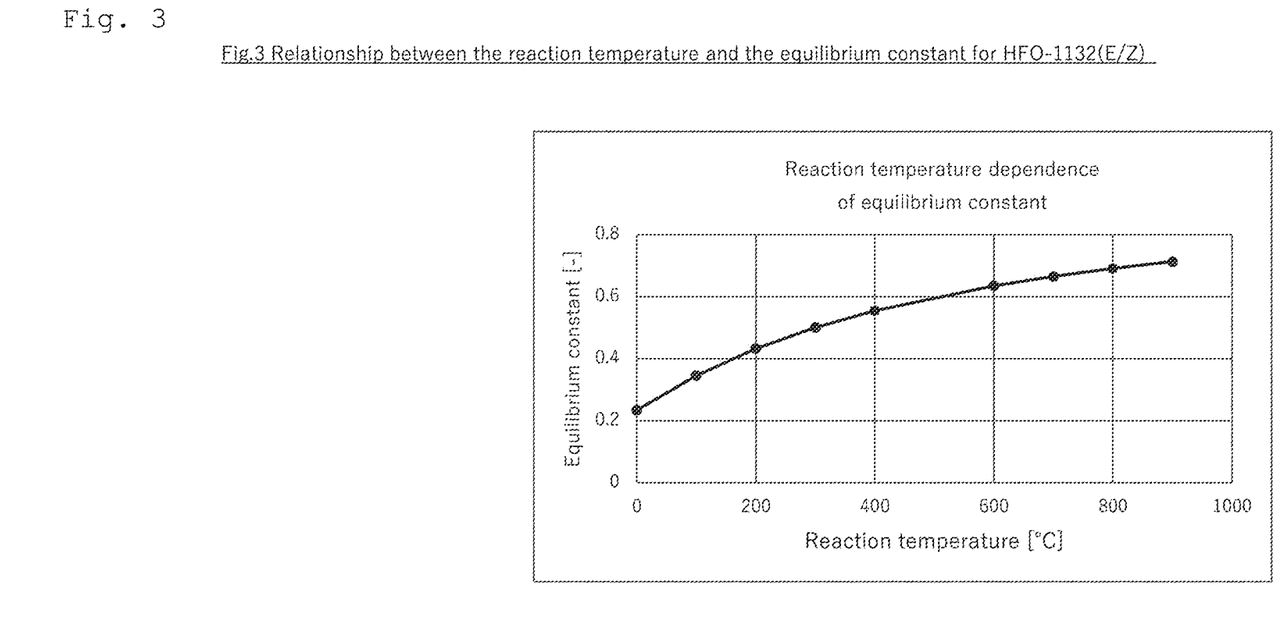
FIG. 3 is a graph illustrating the relationship between the reaction temperature and the equilibrium constant for HFO-1132(E) and HFO-1132(Z) in the method for producing HFO-1132(E) and/or HFO-1132(Z) according to the present disclosure.

Table 3 shows the relationship of the equilibrium constant between HFO-1132(E) and HFO-1132(Z) to the reaction temperature. FIG. 3 is a graphical representation of the values shown in Table 3.

TABLE 3

| Reaction temperature | Equilibrium constant |
|---|---|
| ° C. | — |
| 0 | 0.233839 |
| 100 | 0.345175 |
| 200 | 0.432190 |
| 300 | 0.500311 |
| 400 | 0.554523 |
| 600 | 0.634711 |
| 700 | 0.665064 |
| 800 | 0.690827 |
| 900 | 0.712954 |

Example 3

Method for Producing HFO-1132(Z)

Table 4 shows the relationship between the reaction temperature and the equilibrium ratio of HFO-1132(E) and HFO-1132(Z). When HFO-1132(E) was supplied to a reactor, and an isomerization reaction was performed in particular at a reaction temperature of about 600 to 900° C. without using a catalyst to produce HFO-1132(Z), the proportion of HFO-1132(Z) was large, and the isomerization reaction proceeded well.

TABLE 4

| Temperature | Pressure | Residence time | E/Z ratio | HFO-1132(E) | HFO-R1132(Z) |
|---|---|---|---|---|---|
| ° C. | MPaG | sec | — | — | — |
| 600 | 0.0087 | 0.54 | 15.26699 | 0.93852581 | 0.06147419 |
| 700 | 0.0091 | 0.5 | 1.055249 | 0.51344086 | 0.48655914 |
| 800 | 0.0097 | 0.44 | 0.694452 | 0.40983856 | 0.59016144 |
| 900 | 0.0108 | 0.4 | 0.68777 | 0.40750213 | 0.59249787 |

Example 4

Method for Producing HFO-1132(E)

Table 5 shows the relationship between the reaction temperature and the equilibrium ratio of HFO-1132(E) and HFO-1132(Z). When HFO-1132(Z) was supplied to a reactor, and an isomerization reaction was performed in particular at a reaction temperature of about 600 to 900° C. without using a catalyst to produce HFO-1132(E), the proportion of HFO-1132(E) was large, and the isomerization reaction proceeded well.

TABLE 5

| Temperature | Pressure | Residence time | E/Z ratio | MFG-1132(E) | HFO-R1132(Z) |
|---|---|---|---|---|---|
| ° C. | MPaG | sec | — | — | — |
| 600 | 0.0073 | 0.54 | 0.037799 | 0.03642238 | 0.96357762 |
| 700 | 0.0082 | 0.5 | 0.515197 | 0.34001992 | 0.65998008 |
| 800 | 0.0092 | 0.44 | 0.690149 | 0.4083361 | 0.5916639 |
| 900 | 0.0103 | 0.4 | 0.641221 | 0.39069767 | 0.60930233 |

The invention claimed is:

1. A method for producing trans-1,2-difluoroethylene (HFO-1132(E)) and/or cis-1,2-difluoroethylene (HFO-1132(Z)), the method comprising:
   supplying a composition containing HFO-1132(E) and/or HFO-1132(Z) to a reactor, and performing an isomerization reaction between HFO-1132(E) and HFO-1132(Z) at a reaction temperature of 600° C. or more.

2. The method according to claim 1, wherein the isomerization reaction is performed in the absence of a catalyst.

3. A method for producing trans-1,2-difluoroethylene (HFO-1132(E)) and/or cis-1,2-difluoroethylene (HFO-1132(Z)), the method comprising:
   supplying a composition containing HFO-1132(E) and/or HFO-1132(Z) to a reactor, and performing an isomerization reaction between HFO-1132(E) and HFO-1132(Z) at a reaction temperature of 200° C. or more in the absence of a catalyst.

4. The method according to claim 1, wherein HFO-1132(Z) or a composition containing HFO-1132(E) and HFO-1132(Z) is supplied to the reactor, and HFO-1132(E) is produced in the isomerization reaction.

5. The method according to claim 1, wherein HFO-1132(E) or a composition containing HFO-1132(E) and HFO-1132(Z) is supplied to the reactor, and HFO-1132(Z) is produced in the isomerization reaction.

6. The method according to claim 1, comprising performing separation into HFO-1132(E) and HFO-1132(Z) by distillation after the isomerization reaction.

7. The method according to claim 6, comprising recycling HFO-1132(Z) to the isomerization reaction after the separation step, wherein HFO-1132(Z) or a composition containing HFO-1132(E) and HFO-1132(Z) is supplied to the reactor again, and HFO-1132(E) is produced.

8. The method according to claim 6, comprising recycling HFO-1132(E) to the isomerization reaction after the separation step, wherein HFO-1132(E) or a composition containing HFO-1132(E) and HFO-1132(Z) is supplied to the reactor again, and HFO-1132(Z) is produced.

9. The method according to claim 2, wherein HFO-1132(Z) or a composition containing HFO-1132(E) and HFO-1132(Z) is supplied to the reactor, and HFO-1132(E) is produced in the isomerization reaction.

10. The method according to claim 3, wherein HFO-1132(Z) or a composition containing HFO-1132(E) and HFO-1132(Z) is supplied to the reactor, and HFO-1132(E) is produced in the isomerization reaction.

11. The method according to claim 2, wherein HFO-1132(E) or a composition containing HFO-1132(E) and HFO-1132(Z) is supplied to the reactor, and HFO-1132(Z) is produced in the isomerization reaction.

12. The method according to claim 3, wherein HFO-1132(E) or a composition containing HFO-1132(E) and HFO-1132(Z) is supplied to the reactor, and HFO-1132(Z) is produced in the isomerization reaction.

13. The method according to claim 2, comprising performing separation into HFO-1132(E) and HFO-1132(Z) by distillation after the isomerization reaction.

14. The method according to claim 3, comprising performing separation into HFO-1132(E) and HFO-1132(Z) by distillation after the isomerization reaction.

15. The method according to claim 4, comprising performing separation into HFO-1132(E) and HFO-1132(Z) by distillation after the isomerization reaction.

16. The method according to claim 9, comprising performing separation into HFO-1132(E) and HFO-1132(Z) by distillation after the isomerization reaction.

17. The method according to claim 10, comprising performing separation into HFO-1132(E) and HFO-1132(Z) by distillation after the isomerization reaction.

18. The method according to claim 14, comprising recycling HFO-1132(Z) to the isomerization reaction after the separation step, wherein HFO-1132(Z) or a composition containing HFO-1132(E) and HFO-1132(Z) is supplied to the reactor again, and HFO-1132(E) is produced.

19. The method according to claim 14, comprising recycling HFO-1132(E) to the isomerization reaction after the separation step, wherein HFO-1132(E) or a composition containing HFO-1132(E) and HFO-1132(Z) is supplied to the reactor again, and HFO-1132(Z) is produced.

\* \* \* \* \*